(12) United States Patent
Gahagan et al.

(10) Patent No.: US 7,215,418 B2
(45) Date of Patent: May 8, 2007

(54) INSPECTION OF TRANSPARENT SUBSTRATES FOR DEFECTS

(75) Inventors: Kevin T. Gahagan, Painted Post, NY (US); Jason F. Hiltner, Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/414,076

(22) Filed: Apr. 28, 2006

(65) Prior Publication Data

US 2006/0192952 A1 Aug. 31, 2006

Related U.S. Application Data

(63) Continuation of application No. 10/382,689, filed on Mar. 5, 2003, now Pat. No. 7,142,295.

(51) Int. Cl.
*G01N 21/00* (2006.01)

(52) U.S. Cl. .............................. 356/237.2; 356/239.1; 356/239.2; 356/239.3

(58) Field of Classification Search .. 356/237.1–237.6, 356/239.1, 239.3, 239.6, 239.7, 124.5; 250/223 B, 250/223 R, 561–562, 201.1, 203.1, 559.16
See application file for complete search history.

(56) References Cited

U.S. PATENT DOCUMENTS

| | | | | |
|---|---|---|---|---|
| 3,792,930 A | * | 2/1974 | Obenreder | 356/445 |
| 3,921,080 A | * | 11/1975 | Hardy | 327/7 |
| 3,971,956 A | * | 7/1976 | Jakeman et al. | 250/559.16 |
| 4,129,775 A | * | 12/1978 | O'Meara | 250/203.1 |
| 4,136,961 A | | 1/1979 | Young, II | 356/239 |
| 4,274,747 A | | 6/1981 | Van Beeck et al. | |
| 4,500,203 A | * | 2/1985 | Bieringer | 356/239.4 |
| 4,576,482 A | * | 3/1986 | Pryor | 356/612 |
| 4,943,709 A | * | 7/1990 | Grinberg et al. | 250/201.9 |
| 5,016,099 A | | 5/1991 | Bongardt et al. | 358/106 |
| 5,059,023 A | * | 10/1991 | Task | 356/239.1 |
| 5,220,178 A | * | 6/1993 | Dreiling et al. | 250/559.03 |
| 5,355,213 A | | 10/1994 | Dotan | |
| 5,452,079 A | | 9/1995 | Okugawa | 356/237 |
| 5,598,262 A | * | 1/1997 | Jutard et al. | 356/239.1 |
| 5,684,545 A | * | 11/1997 | Dou et al. | 349/1 |
| 5,691,811 A | | 11/1997 | Kihira | 356/237 |
| 5,764,345 A | | 6/1998 | Fladd et al. | 356/35.5 |
| 5,880,843 A | * | 3/1999 | Hermosillo-Valadez et al. | 356/600 |
| 5,907,396 A | * | 5/1999 | Komatsu et al. | 356/237.1 |
| 6,011,620 A | | 1/2000 | Sites et al. | 356/239.1 |
| 6,075,591 A | | 6/2000 | Vokhmin | 356/239.1 |
| 6,359,686 B1 | | 3/2002 | Ariglio et al. | |
| 6,369,888 B1 | * | 4/2002 | Karpol et al. | 356/237.5 |
| 6,388,745 B2 | | 5/2002 | Stevens | 356/239.7 |
| 6,495,833 B1 | | 12/2002 | Alfano et al. | |

(Continued)

FOREIGN PATENT DOCUMENTS

DE 3611574 A1 * 10/1987

(Continued)

*Primary Examiner*—Sang H. Nguyen
(74) *Attorney, Agent, or Firm*—Christopher Nicastri; William J. Tucker (57) ABSTRACT

Methods, apparatus and systems for the detection of defects in transparent substrates such as glass sheets are disclosed. The methods, apparatus and systems are capable of detecting optical path length variations in transparent substrates smaller than 100 nm.

23 Claims, 5 Drawing Sheets

U.S. PATENT DOCUMENTS

| | | | |
|---|---|---|---|
| 6,522,777 B1 | 2/2003 | Paulsen et al. | |
| 6,628,379 B1 * | 9/2003 | Sudo et al. | 356/237.1 |
| 6,816,247 B1 * | 11/2004 | Heppner et al. | 356/124 |
| 2002/0057429 A1 | 5/2002 | Okahira et al. | |

FOREIGN PATENT DOCUMENTS

| | | |
|---|---|---|
| EP | 0559433 A1 | 3/1993 |
| EP | 0576011 A1 | 6/1993 |
| JP | 05005854 A * | 1/1993 |
| WO | WO 99/51971 | 10/1999 |

* cited by examiner

INSPECTION OF TRANSPARENT SUBSTRATES FOR DEFECTS

CROSS-REFERENCE TO RELATED APPLICATION

This application is a continuation of U.S. application Ser. No. 10/382,689, filed on Mar. 5, 2003 now U.S. Pat No. 7,142,295 the content of which is relied upon and incorporated herein by reference in its entirety, and the benefit of priority under 35 U.S.C. §120 is hereby claimed.

FIELD OF THE INVENTION

This invention relates to systems, methods and apparatus for the inspection of substrates to determine defects. The invention is particularly useful for the measurement of one dimensional optical path length variations in glass sheets.

BACKGROUND OF THE INVENTION

Defects in transparent substrates such as glass sheets are typically detected utilizing human inspectors and manual methods. For example, in the detection of defects such as cord and streak in glass substrates used in liquid crystal displays (LCDs), a shadow method is used to detect the defects. According to this method, a sheet of glass (typically about 1 meter wide×2 meters long) is mounted in a freely rotating L-bracket stand and illuminated by a xenon light source. The light source is diverging to illuminate the entire sheet. The shadow of the glass is viewed on a white screen by an inspector. The defects appear as one dimensional lines of contrast on the screen. The direction of the lines is parallel to the direction the glass sheets are drawn, for example in a downdraw apparatus in which glass sheets are manufactured. Streak defects typically appear as a single isolated line, whereas cord defects consist of multiple lines spaced every few millimeters.

Cord defects typically consist of optical path length (OPL) variations as small as a few nanometers with periods of a few millimeters. These small variations, resulting from thickness or refractive index variations, modulate the light intensity on the screen by an effect commonly referred to as lensing. Repeatable and reliable visual inspection of cord and streak defects has proven to be extremely difficult, especially using manual methods. Accordingly, it would be desirable to provide apparatus, systems and methods capable of measuring one-dimensional optical path length variations of transparent substrates.

SUMMARY OF INVENTION

The invention relates to apparatus, methods and systems for measuring optical path length variations in transparent substrates such as glass sheets. The invention can be used to measure variations in thickness in transparent substrates. Streak defects and dust can be distinguished from cord more easily than in presently existing methods.

According to some embodiments of the invention, optical path length variations are observed indirectly by illuminating the glass with a highly spatially coherent beam. Interference effects that can complicate interpretation of the contrast pattern are reduced by use of a temporally incoherent beam, i.e. one with a very short coherence length. According to certain embodiments, if the OPL variations have a period less than or about equal to the beam size, the optical path length variation causes phase distortion in the beam which can be measured, thus providing a physical effect related to the variation of the path length (on a scale of about 10 nm.)

In certain preferred embodiments, measurement of the phase distortion is accomplished by spatially filtering the light, for example, by using a superluminescent diode (SLD) light source coupled to single-mode fiber. The SLD preferably has a wavelength spectrum wide enough to provide a coherence length shorter than the optical path length through the glass, to reduce interference effects. High spatial coherence can be provided by the use of single-mode fiber. Preferably, the beam is launched from fiber, and a lens placed one focal length away from the fiber end produces a collimated beam. Instead of using an optical fiber, spatial filtering may also be accomplished by transmitting the light through a small opening, preferably less than 50 microns in diameter, and preferably less than about 20 microns.

According to certain embodiments, the light source is directed through the sample of interest at normal incidence, and a positive lens is used to partially focus the beam onto a slit. Preferably, the slit is placed in front of the focal plane of the lens. According to one aspect, phase distortion from defects in the substrate results in small changes in the intensity profile of the beam at the slit position. A sensor placed behind the slit detects the light intensity passing through the slit. In some embodiments, by translating the entire optical system across the glass, changes in phase distortion in the beam are measured as contrast in the light intensity versus position data. Local variations in the optical path length of the glass can then be inferred from this data. According to some embodiments, two spaced apart light sources are used to allow contrast in the signal which is due to one dimensional defects (i.e. cord or streak) to be distinguished from other more localized defects, which can include dust, inclusions, etc. Once the light intensity as a function of the glass position is acquired, an algorithm processes the data to quantify the contrast in the signal.

The present invention has wider spatial frequency response range resulting in higher resolution of defects on the glass surface than in prior art systems. The invention provides a repeatable measurement that is sensitive to low level defects (e.g., less than about 100 nm, preferably less than about 50 nm and as small as about 1 nm OPL variations). The system and apparatus are compact and can rapidly measure defects.

Additional advantages of the invention will be apparent from the following detailed description. It is to be understood that both the foregoing general description and the following detailed description are exemplary and are intended to provide further explanation of the invention as claimed.

DETAILED DESCRIPTION

Before describing several exemplary embodiments of the invention, it is to be understood that the invention is not limited to the details of construction or method steps set forth in the following description. The invention is capable of other embodiments and of being practiced or carried out in various ways.

The present invention relates to apparatus, systems and methods for inspecting transparent substrates such as glass sheets. The invention is particularly useful for detecting one dimensional OPL variations on the order of about 100 nm or less, for example, less than about 50 nm or 10 nm, and as small as about 1 nm on liquid crystal display substrates.

Figure 1:
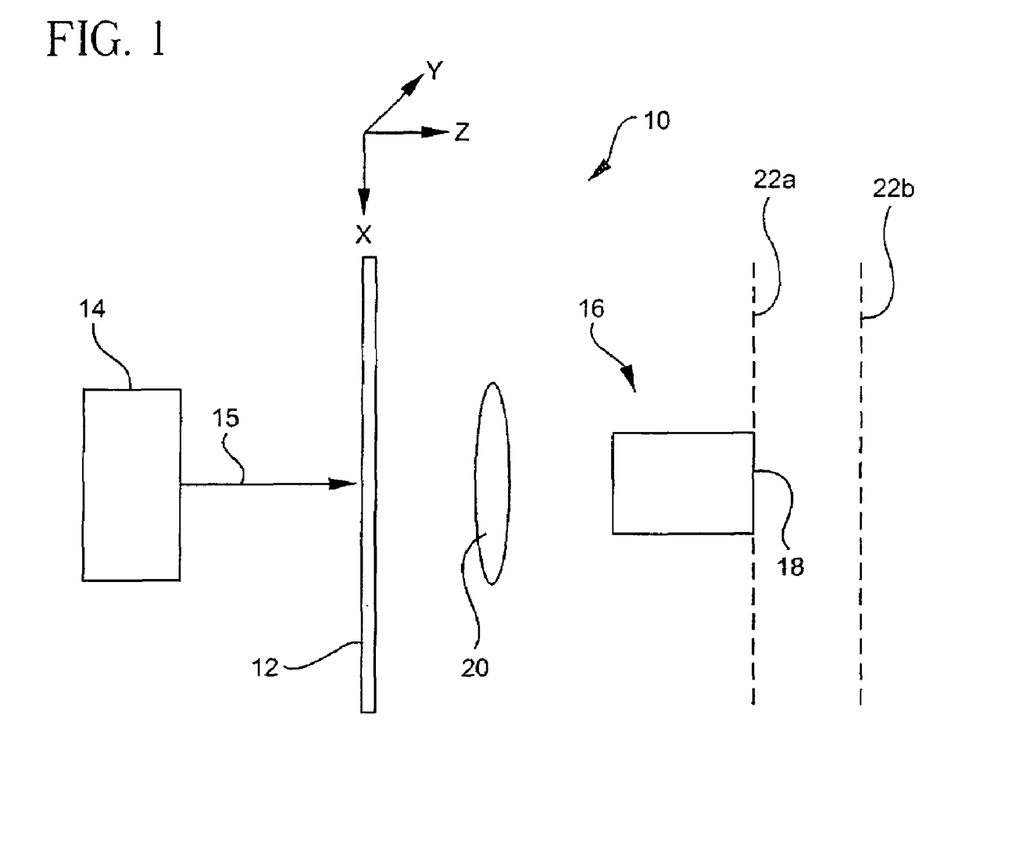
FIG. 1 shows a schematic representation of an apparatus for measuring defects in transparent substrates according to one embodiment of the invention.
Figure 2:
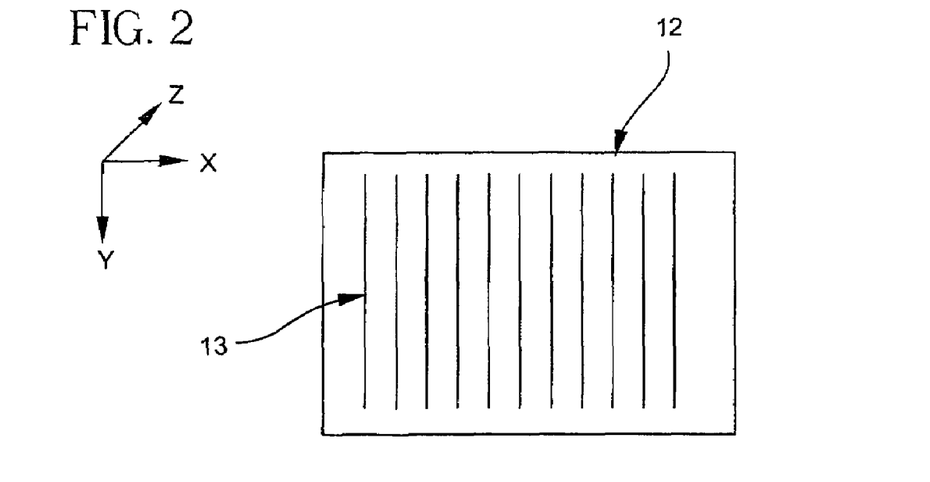
FIG. 2 is a drawing of a glass sheet having a cord defect.

Referring to FIG. 1 and according to a first embodiment of the invention, an apparatus 10 for measuring defects in or on transparent substrates 12 is provided. The apparatus is particularly useful for measuring cord defects in glass substrates used in liquid crystal displays. As shown in FIGS. 1 and 2, the optical path length through the glass sheet, measured along the z-direction, varies with position along the "x" axis, resulting in a pattern of features, typically called cord or streak, oriented parallel to the draw direction or the "y" axis indicated in FIG. 2. The modulation of the optical path length along "x" is periodic with periods in the range of a about few millimeters and amplitudes in the range of about a few nanometers. Still referring to FIGS. 1 and 2, the apparatus 10 includes a first light source 14 for directing a first beam of light 15 at the substrate 12. Preferably, the first light source 14 is directed at the substrate 12 so that the first beam of light 15 travels in a direction substantially normal to the sheet, parallel to the "z" axis in FIG. 1. Preferably, the light source 14 is configured so that it can direct light at a plurality of different locations across a planar surface of the substrate 12. Thus, in preferred embodiments the light source can move in the "x" or "y" direction, or alternatively, the substrate 12 can be moved while the light source remains stationary so that light is transmitted towards the surface of the substrate 12 at a plurality of different locations. In a preferred embodiment, the substrate is mounted so the direction of the cord defect runs parallel to the "y" direction shown in FIGS. 1 and 2 and the substrate 12 or the light source 14 moved so that the beam of light translates across the substrate in the "x" direction.

Still referring to FIG. 1, the apparatus 10 further comprises an optical system 16 including at least a first sensor 18 for detecting phase distortion of light transmitted through or reflected from the sheet 12 at different locations. The phase distortion of the light is related to the contrast of light intensity at the different locations across the planar surface of the substrate 12. The optical system preferably includes a first lens 20 between the light source 12 and the sensor 18, the first lens 20 providing the ability to selectively enhance contrast of the phase distortion received at the sensor 18. According to another embodiment, the sensor 18 images a virtual plane 22a or 22b located at (22a) or beyond (22b) the sensor 18., As used herein, beyond the sensor means the plane is in direction moving away from the first light source 14 in the z plane. Thus, as shown in FIG. 1, the light source 14 is on the left, and the sensor 18 is on the right, and a virtual plane 22b located beyond the first sensor 18 would be to the right of the first sensor 18.

Figure 3:
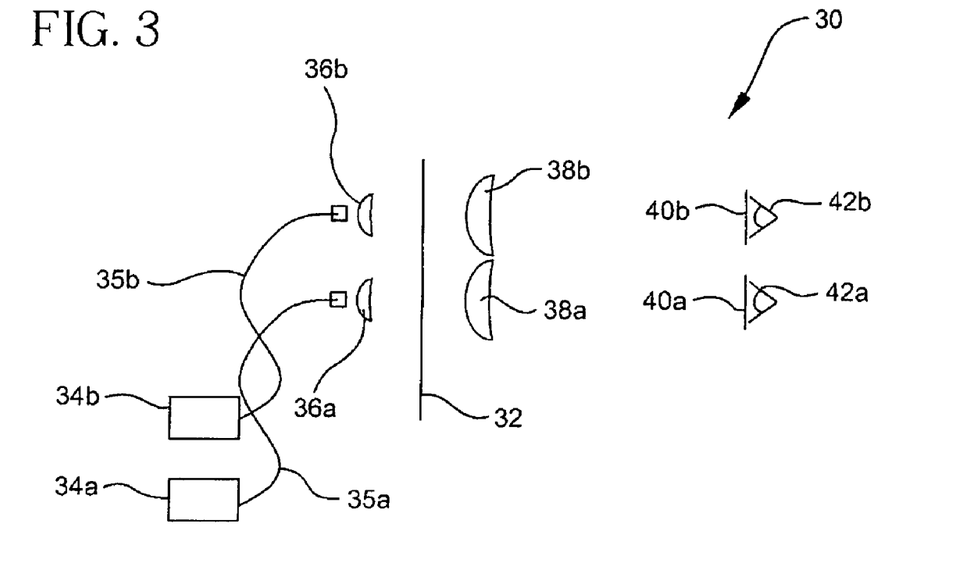
FIG. 3 shows a schematic of an apparatus for measuring defects in transparent substrates according to one embodiment of the invention.

Referring now to FIG. 3, another embodiment of an apparatus 30 for measuring defects in a transparent substrate 32 is shown. The apparatus includes a pair of light sources 34a, 34b in a spaced apart relationship. The light sources can be spaced apart by about 20 mm to 120 mm. In preferred embodiments, each light source 34a, 34b is coupled to a spatial filter. In this embodiment, the spatial filtering is provided by a pair of optical fibers 35a, 35b. Light exits the fibers 35a, 35b which are spaced apart by at least the diameter of the beams of light preferably by about 30 mm and is transmitted through the substrate 32. In preferred embodiments, the beams of light from the light sources 34a and 34b are transmitted through a pair of collimating lenses 36a, 36b, which are disposed between the ends of the fibers 35a, 35b and the substrate 32. After the light is transmitted through the substrate 32, an optical system including a pair of lenses 38a, 38b, referred to hereafter as contrast enhancement lenses or contrast lenses, direct light through a pair of slits 40a, 40b and to sensors 42a, 42b. The optical system is operable to selectively enhance contrast of the phase distortion received at the sensor. As in the previously described embodiment, the sensors 42a, 42b image a virtual plane located at or beyond the sensors 42a, 42b. Additional details of the light source and optical system are described below.

In preferred embodiments, the light source has a coherence length less than the optical thickness of the substrate being measured to avoid interference effects created by reflections from the two major surfaces of the planar substrate. Preferably the light source is spatially coherent as well. Spatial coherence means that the phase front perpendicular to the beam propagation direction ("z" plane in FIG. 1) is uniform across the beam. Spatial coherence can be achieved by spatially filtering a light source. Spatial filtering can be achieved by transmitting light through a small opening at least about ten times smaller and preferably 40 times smaller than the smallest lateral defect dimension of interest, or by using a source that has been coupled to single mode fiber.

Figure 4:
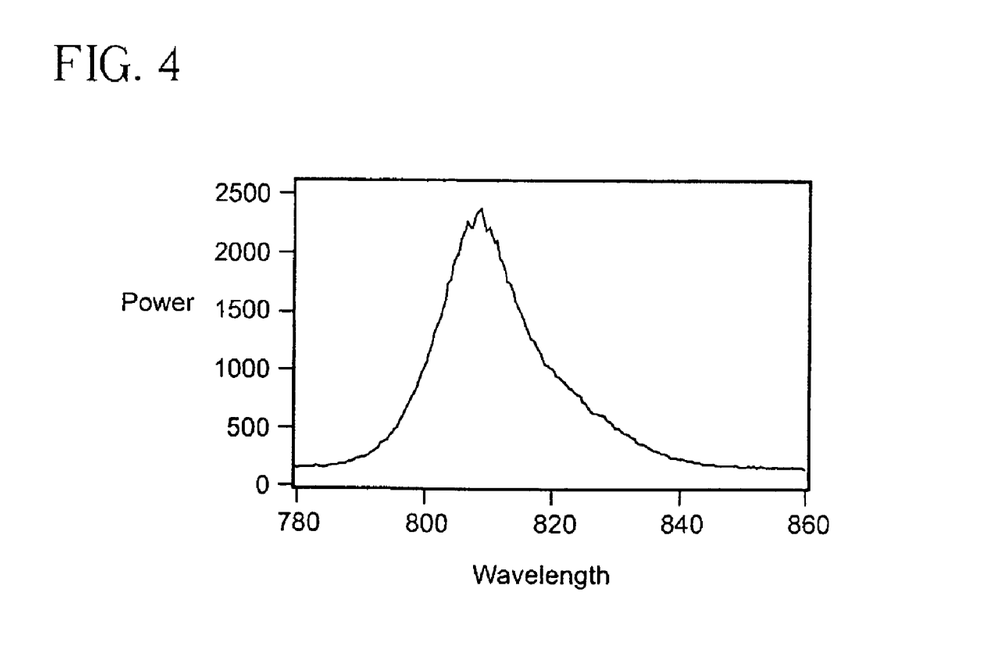
FIG. 4 is a graph showing the output spectrum of a light source according to one embodiment.

A particularly preferred light source is a superluminescent diode (SLD). This device provides temporally-incoherent (relatively wide wavelength spectrum) light. FIG. 4 shows the output spectrum of a superluminescent diode in arbitrary power units according to one embodiment of the invention, which corresponds to a coherence length of less than about 50 □m. While many types of broadband sources can provide short coherence lengths (tungsten-halogen, xenon, LED's, etc.), the SLD can be coupled very efficiently into a single-mode fiber. This allows for efficient spatial filtering of the light source while retaining reasonable power levels (about 1 mW out of the fiber). Spatial filtering of more typical light sources results in unacceptably low power. Levels of contrast characteristic of cord and streak defects are on the order of 1% or less. Hence, the excellent power stability of SLD sources (e.g., less than 0.05% over about 10 seconds) is preferred.

Preferably, the light emerging from the spatial filter is collimated prior to being incident on the substrate. Collimation of the light beam reduces system sensitivity to sheet position and motion along the direction of beam propagation and also simplifies interpretation of the data collected by the sensor. In a preferred embodiment, the incident light beam is collimated to a diameter of about 5–20 mm ($1/e^2$ diameter). The beam size sets an upper limit on the period of optical-path-length variations to which the system is sensitive. A relatively large beam size results in a system that is sensitive to streak (with typical widths less than about 5 mm), while being insensitive to longer period changes in substrate optical path length variation.

In preferred embodiments, two light sources are used and placed in a spaced apart relationship as shown in FIG. 3. Two beam paths in a system reduce errors in measurement resulting from dust and other contamination on the surface of the substrate. In preferred embodiments, the beams are offset vertically (along the y axis of the substrate or parallel to the cord/streak direction) to sample different areas of the glass surface so that contrast common to both beams is purely due to cord or streak. Contrast differences measured by only one beam can be affected by dust, pen marks, inclusions or defects internal to the glass. The offset of the beams should be small enough to ensure that differences in the cord/streak features sampled by the two beams are minimal. This will be constrained by how rapidly the cord or streak features vary along the y-axis. Two beams of light could be produced by a single light source and a beam splitter and mirror to provide the two beams. An example of a beam-splitting device is a fiber optic coupler. However, for better long term stability, two separate sources (one source for each beam of light) are preferred.

As noted above, a lens incorporated into the system and placed between the substrate and the sensor enhances the contrast resulting from cord and streak, while also resulting in a shorter path optical system. However, factors such as vibration and alignment sensitivity limit the use of shorter focal length lenses. For example, a 50 mm to 400 mm focal length lens provides a good combination of contrast enhancement while maintaining insensitivity to vibration.

Figure 5:
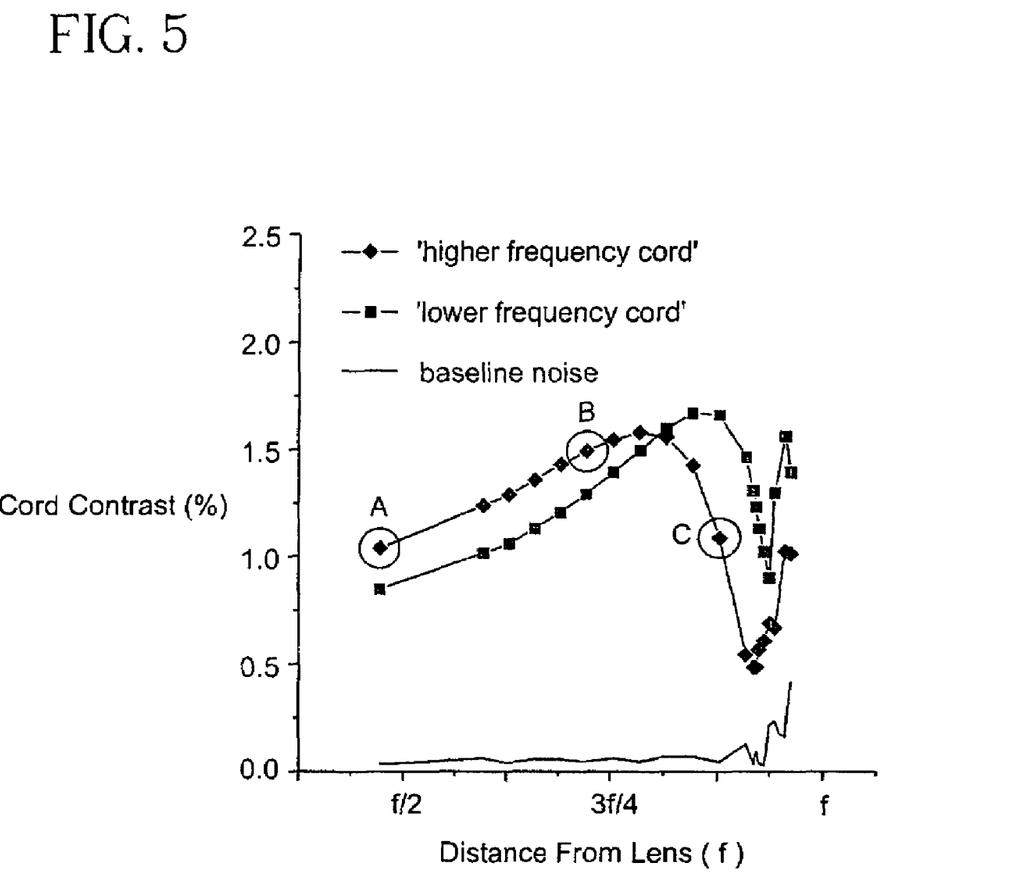
FIG. 5 is a graph showing actual measured cord contrast percentage versus lens to slit distance according to one embodiment of the invention.

The spatial frequency sensitivity of the system or apparatus may be optimized for a particular range by adjusting the distance between the lens and the plane at which the intensity contrast is measured, defined by the location of the slit, placed between the lens and sensor, in some preferred embodiments. An example of the frequency dependence of the optical system measured under different configurations is shown in FIG. 5. FIG. 5 shows the measured contrast obtained using a lens of focal length (f) and a ten micron slit, for two cord defects with different periods. As the slit is moved away from the lens (moved closer to the focal point of the lens) the contrast for each pattern increases, reaches a peak contrast, and then rapidly decreases as the slit position nears the focal point. The peak contrast for higher frequency cord patterns (shorter period) occurs at a plane closer to the lens.

The circles marked A, B and C in the FIG. 5 show several possible choices for optimized optical system design. The circle A is a point of least contrast enhancement, but broadest frequency response. The circle B has the highest contrast enhancement for the lower frequency peak, but reduced contrast for the high frequency peak. The circle C is a preferred operating point. This point represents a tradeoff, where contrast enhancement is produced without decreasing the relative response of the highest observed frequency cord.

The width of a slit placed between the lens and the sensor is preferably narrow enough to fully resolve the highest frequency contrast features, but wide enough to pass enough light power to the sensor to maintain signal to noise ratio. To prevent errors in measurement, preferably the slit is aligned substantially parallel to the direction of the cord defect. By substantially aligned, the slit should be aligned to within about 0.5 degrees of the direction of the cord.

A preferred sensor is a silicon photodiode with a minimum area of about 4 mm×1 mm. Preferably, each slit is coupled directly to the surface of the sensor. The photodiode produces a current which is directly proportional to the light power that passes through the slit. This current is on the order of about 10 □A, and preferably the current is amplified by a low-noise transimpedance amplifier. However, the invention is not limited to any particular sensor. Other suitable sensors include, but are not limited to, a charge coupled device (CCD) or other types of photosensitive sensors.

The data from the sensors is acquired and analyzed using conventional electronics and data processing equipment, for example, a computer. Preferably, the voltages produced by the sensors are digitized using an analog to digital converter. The processor would categorize defects (e.g., streak versus cord and dust) and quantify the magnitude of the defects. The data is then related and analyzed to quantify OPL variations through the sample.

Figure 6:
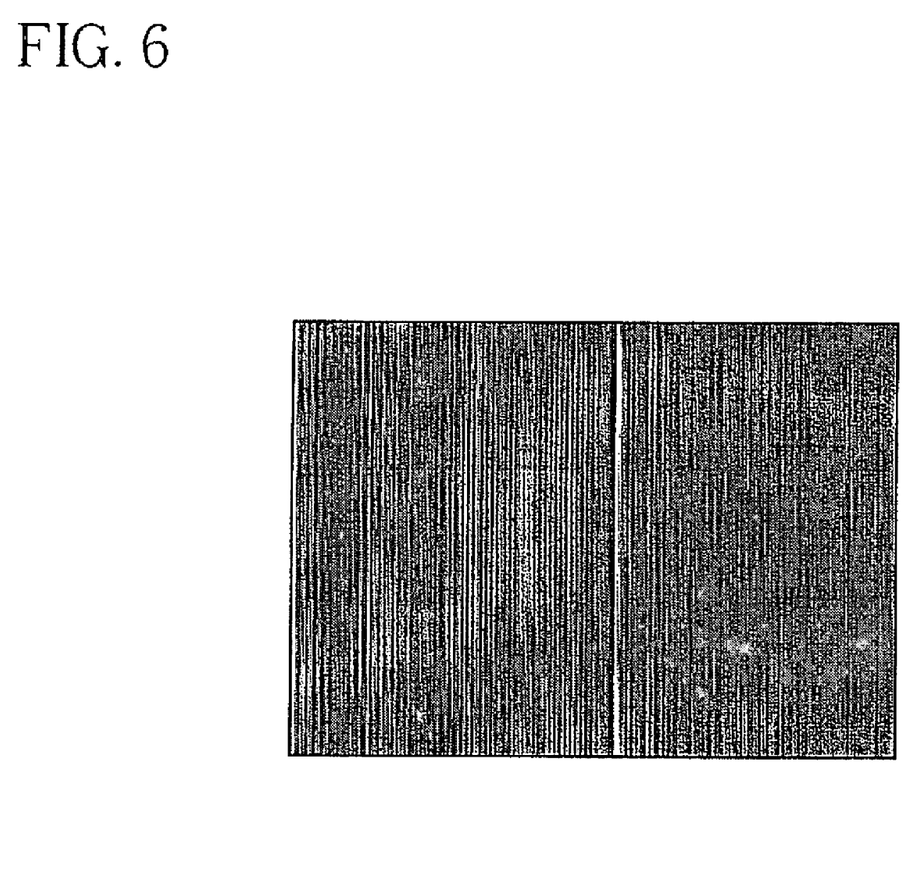
FIG. 6 is a two dimensional projection of line scan data acquired from a system after scanning a glass sheet containing cord and streak defects according to one embodiment of the invention.

An example of data acquired from an apparatus according to one embodiment is shown in FIG. 6, which shows measured contrast across a sample at a scan rate of about 100 mm/second. FIG. 6 is a 2D representation of line scan data, where the contrast has been enhanced, and cord appears as periodic lines of contrast. The y and x axes of FIG. 6 correspond to the y and axes of a glass sheet described in FIG. 3. In FIG. 6, cord is evident as a period change in intensity across the image, and a streak defect is evident as a bright, isolated line near the center of the image.

The overall repeatability of the system of the present invention is excellent. Results from a repeatability and reproducibility study for samples containing cord and streak and measured by the system of the present invention showed good correlation to the graded defect severity (as judged by manual inspection). Positional dependence of the system can be minimized by fixing the position of the sensor relative to the light source, and translating the entire optical system across the glass. Streak detection is made possible by creating a dual beam system. Through optimization of the light source and the use of a lens, the system is sensitive enough to detect all known cord defects at normal incidence. In particular, detection of high frequency defects is possible.

Figure 7:
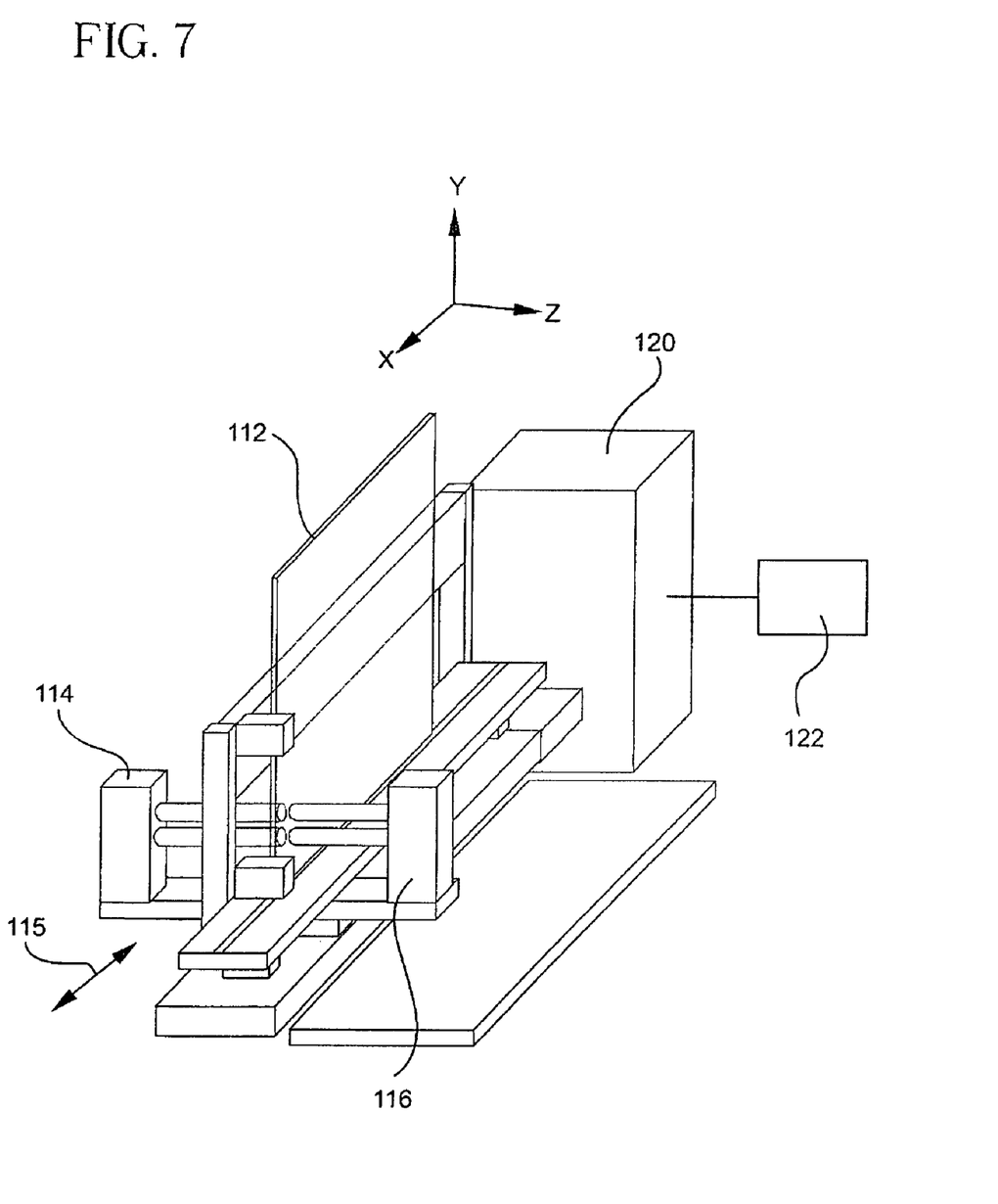
FIG. 7 shows a perspective view of an apparatus for measuring defects in transparent substrates according to one embodiment of the invention.

The system of the present invention is capable of offline inspection in a factory environment. The basic technique is also capable of the data rate required for online inspection. FIG. 7 shows an example of system 100 that can be used to measure substrates 112. The system includes a pair of light sources 114 and a pair of sensors 116 in a spaced apart relationship and fixed with respect to each other. Preferably, each light source and sensor are spaced apart by less than about 1 meter, and preferably less than about 0.5 meters, and more preferably, less than about 30 cm. The substrate 112 can be moved with respect to the light sources and sensors, or alternatively, the light sources and sensors can be mounted to a movable stage and translated across the sheet in the direction shown by arrow 115. Data acquired by the sensors 116 is communicated to an electronics pack, which is in communication with a data processor 122. The data processor can be any conventional data processor such as a personal computer or mainframe computer. The measurement system is relatively insensitive to glass vibration, does not require very stringent glass positioning, and is tolerant to dust effects.

It will be apparent to those skilled in the art that various modifications and variations can be made to the present invention without departing from the spirit or scope of the invention. For example, response to higher spatial frequencies can be obtained by either eliminating the lens or moving the slit closer to the lens. Higher contrast due to the defects can be obtained by moving the slit closer to the focal point of the contrast lens. A shorter (more compact) overall optical system can be obtained by using a shorter focal length lens on the detection side, which may result in higher sensitivity to vibration effects. While the preferred embodiments showed collection of data from a light beam transmitted through a sample, the system, methods and apparatus could utilize data collected from light beams reflected from the surface of the sample. Collection of both a reflected and transmitted signal by use of a second sensor assembly permits independent measurement of the surface height deviation of both surfaces. It is intended that the present invention cover modifications and variations of this invention provided they come within the scope of the appended claims and their equivalents.

What is claimed is:

1. An apparatus for measuring defects in transparent planar substrates comprising:
    a first spatially coherent and spectrally tailored light source for directing light at the substrate at different locations across a major surface of the substrate; and
    an optical system including a first lens and a first sensor that detects phase distortion of light transmitted through or reflected from the substrate at the different locations, the phase distortion related to contrast of light intensity versus position at the different locations on the substrate, the first lens positioned along an optical path between the first spatially coherent and spectrally tailored light source and the first sensor, the first lens positioned relative to the first sensor such that the first sensor is located at a point on the optical path which is before a focal point of the first lens.

2. The apparatus of claim 1, wherein the first sensor is operable to measure the light intensity at a virtual plane located at or beyond the first sensor.

3. The apparatus of claim 2, wherein the apparatus is capable of measuring one dimensional optical path length variations of about 10 nm.

4. The apparatus of claim 1, wherein the first spatially coherent and spectrally tailored light source includes a light source and a spatial filter.

5. The apparatus of claim 4, wherein the spatial filter includes a small opening through which the light is transmitted.

6. The apparatus of claim 5, wherein the opening has a diameter less than about 50 microns.

7. The apparatus of claim 5, wherein the opening has a diameter less than about 20 microns.

8. The apparatus of claim 4, wherein the spatial filter includes an optical fiber.

9. The apparatus of claim 8, wherein the optical fiber is a single mode optical fiber.

10. The apparatus of claim 9, wherein the light source has low temporal coherence.

11. The apparatus of claim 10, wherein the coherence length of the light source is less than the optical path length through the substrate.

12. The apparatus of claim 11, wherein the coherence length of the light source is less than about 50 microns.

13. The apparatus of claim 12, wherein the light source includes a superluminescent diode.

14. The apparatus of claim 1, wherein the positions of the first spatially coherent and spectrally tailored light source and the first sensor are fixed in relation to each other.

15. The apparatus of claim 14, wherein first spatially coherent and spectrally tailored light source and the first sensor are translated across the plane of the substrate.

16. The apparatus of claim 15, wherein the substrate is located between the first spatially coherent and spectrally tailored light source and the first sensor.

17. The apparatus of claim 16, wherein the spacing between the first spatially coherent and spectrally tailored light source and the first sensor is less than about 1 meter.

18. The apparatus of claim 17, wherein the spacing between the first spatially coherent and spectrally tailored light source and the first sensor is less than 30 cm.

19. The apparatus of claim 1, further comprising a second spatially coherent and spectrally tailored light source spaced apart from the first spatially coherent and spectrally tailored light source, a second sensor spaced apart from the first sensor, and a second lens spaced apart from the first lens.

20. An apparatus for measuring defects in transparent planar substrates comprising:
    a first light source for directing light at the substrate at different locations across a major surface of the substrate; and
    an optical system including a first contrast enhancement lens and a first sensor that detects phase distortion of light transmitted through the substrate at the different locations, the phase distortion related to contrast of light intensity versus position at the different locations on the substrate, the first contrast enhancement lens positioned along the optical path between the first light source and the first sensor, the first contrast enhancement lens operable to selectively enhance the intensity contrast of the light received at the first sensor;
    a first optical fiber coupled to the first light source for spatially filtering the light directed at the substrate;
    a first collimating lens disposed between the first optical fiber and the substrate for collimating the beam of light transmitted through the substrate; and
    said optical system including a first slit disposed between the first contrast enhancement lens and the first sensor, wherein the first slit has an opening size of at least 10 microns and is located in front of the focal point of the first contrast enhancement lens.

21. The apparatus of claim 20, further comprising a second light source spaced apart from the first light source, a second optical fiber spaced apart from the first optical fiber, a second collimating lens spaced apart from the first collimating lens, a second contrast enhancement lens spaced apart from the first contrast enhancement lens, a second slit spaced apart from the first slit, and a second sensor spaced apart from the first sensor.

22. An apparatus for measuring defects in a glass substrate comprising:
    a pair of superluminescent diodes coupled to a pair of single mode optical fibers for producing a pair of light beams directed at the substrate;
    a pair of collimating lenses disposed between the substrate and the superluminescent diodes; and
    an optical system including a pair of contrast enhancement lenses, a pair of slits, and a pair of sensors that detect phase distortion of light transmitted through or reflected from the substrate at the different locations, the phase distortion related to contrast of light intensity versus position at the different locations on the substrate, the contrast enhancement lenses positioned along an optical path between the superluminescent diodes and the sensors, the slits positioned between the sensors and the contrast enhancement lenses, the first contrast enhancement lens positioned relative to the first slit and the first sensor such that both the first slit and the first sensor are located before a focal point of the first contrast enhancement lens, and the second contrast enhancement lens positioned relative to the second slit and the second sensor such that both the second slit and the second sensor are located before a focal point of the second contrast enhancement lens.

23. The apparatus of claim 22, wherein the pair of diodes and pair of sensors are fixed in relation to each other and the substrate is translated with respect to the diodes and the sensors.

* * * * *